(12) United States Patent
Closson et al.

(10) Patent No.: US 7,678,749 B2
(45) Date of Patent: Mar. 16, 2010

(54) ORGANOLEPTIC COMPOUNDS

(75) Inventors: Adam Closson, Red Bank, NJ (US); Michael G. Monteleone, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 188 days.

(21) Appl. No.: 11/958,038

(22) Filed: Dec. 17, 2007

(65) Prior Publication Data

US 2009/0156456 A1    Jun. 18, 2009

(51) Int. Cl.
*C11D 3/50* (2006.01)

(52) U.S. Cl. .......................... 510/103; 512/9; 549/341; 568/374

(58) Field of Classification Search .................. 510/103; 512/9; 549/341; 568/374
See application file for complete search history.

(56) References Cited

OTHER PUBLICATIONS

X. Dai et al., Advanced Synthesis and Catalysis 2006, vol. 348, issues 16+ 17, pp. 2449-2456, Aug., 2006. Abstract.*

M.T.M. Clements et al., Canadian Journal of Chemistry, 1988, vol. 66, issue 3, pp. 454-460. No month available. Abstract.*

* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention is directed to the fragrance compounds and their intermediates and a method of improving, enhancing or modifying a fragrance formulation through the addition of an olfactory acceptable amount

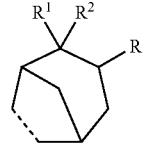

wherein the dotted line represents a possible single or double bond; wherein R is equal to a $C_3$-$C_7$ hydrocarbon moieties $R^1$ and $R^2$ together can be selected from the group consisting of oxygen and may form a closed ring structure represented by

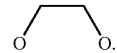

12 Claims, No Drawings

ORGANOLEPTIC COMPOUNDS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

One embodiment of the invention is directed to a fragrance compound and a method of improving, enhancing or modifying a fragrance formulation through the addition of an olfactory acceptable amount of the following formula:

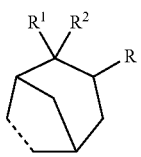

wherein the dotted line represents a possible single or double bond; wherein R is selected from the group consisting of a $C_3$-$C_7$ hydrocarbon moiety and $R^1$ and $R^2$ together can be selected from the group consisting of oxygen and may form a closed ring structure represented by

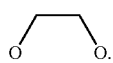

In another embodiment, the present invention is directed to the fragrance compounds and a method of improving, enhancing or modifying a fragrance formulation through the addition of an olfactory acceptable amount the following formula:

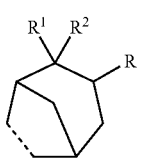

wherein the dotted line represents a possible single or double bond; wherein R is selected from the group consisting of a $C_3$-$C_7$ hydrocarbon moiety, such as C3H and $R^1$ and $R^2$ together can be selected from the group consisting of oxygen and may form a closed ring structure represented by

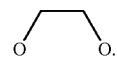

In another embodiment of the invention the use of these materials as a fragrance chemical to enhance fragrance in perfumes, toilet waters, colognes, personal products and the like is also disclosed.

In an additional embodiment of the invention, a method for enhancing a perfume composition by incorporating an olfactory acceptable amount of the compounds provided above is disclosed.

In yet another embodiment of the invention is directed to the following intermediate compounds having the formula:

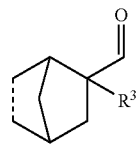

wherein $R^3$ is selected from the group consisting of $C_3$-$C_7$ straight chain hydrocarbon moiety and the dotted line may represent a single or double bond.

These and other embodiments of the present invention will be apparent by reading the following specification.

DETAILED DESCRIPTION OF THE INVENTION

According to the present invention, suitable straight hydrocarbon moieties include ethyl, propyl, butyl, pentyl, hexyl, heptyl, octyl and the like. Suitable branched hydrocarbon moieties include isopropyl, sec-butyl, tert-butyl, 2-ethyl-propyl, and the like. Suitable hydrocarbon moieties containing double and triple bonds include ethene, propene, 1-butene, 2-butene, penta-1-3-deine, hepta-1,3,5-triene, butyne, hex-1-yne and the like. Suitable cyclic hydrocarbon moieties include cyclopropyl, cyclobutyl, cyclopentyl, cyclohexyl and the like.

In the preferred embodiment of the invention, the novel compounds of the present invention are represented by the following structures:

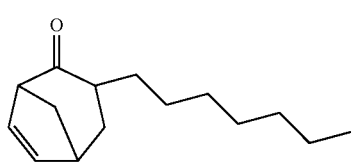

Structure IV

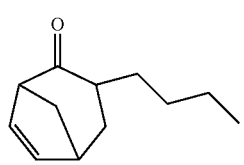

Structure VIII

-continued

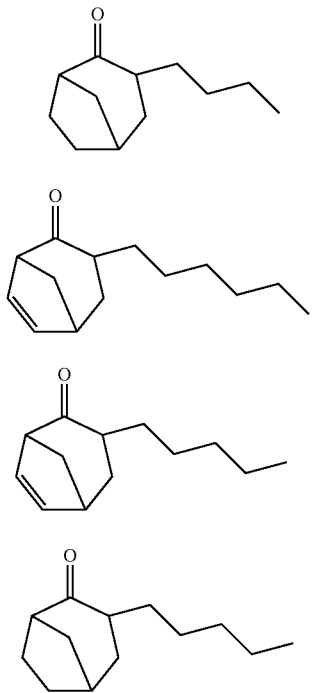

Structure IX

Structure XIII

Structure XVIII

Structure XIX

Those with skill in the art will recognize that Structure IV is 3-heptylbicyclo[3.2.1]oct-6-en-2-one, Structure VIII is 3-butylbicyclo[3.2.1]oct-6-en-2-one, Structure IX is Bicyclo[3.2.1]octan-2-one, 3-butyl, Structure XVIII is 3-pentylbicyclo[3.2.1]oct-6-en-2-one, Structure XIX is Bicyclo[3.2.1]octan-2-one, 3-pentyl and Structure XIII is 3-hexylbicyclo[3.2.1]oct-6-en-2-one.

In another embodiment of the invention the following compounds of the present invention are represented by the following structure:

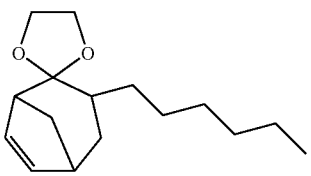

Structure XIV is known by one skilled in the art as Spiro[bicyclo[3.2.1]oct-6-ene-2,2'-[1,3]dioxoloane], 3-hexyl.

The intermediate compounds of the present invention are listed below:

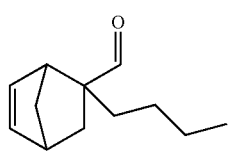

Structure VII

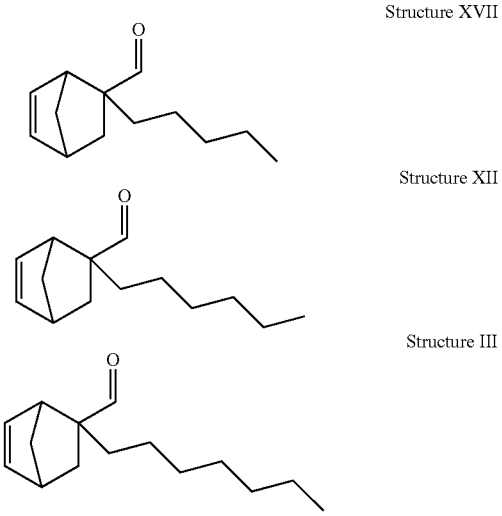

Structure XVII

Structure XII

Structure III

Those with skill in the art will recognize that Structure VII is 3-pentylbicyclo[3.2.1]oct-6-en-2-one; Structure XVII is 2-pentylbicyclo[2.2.1]hept-5-ene-2-carbaldehyde, Structure XII is 2-hexylbicyclo[2.2.1]hept-5-ene-2-carbaldehyde and Structure III is 2-heptylbicyclo[2.2.1]hept-5-ene-2-carbaldehyde Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The compounds of the present invention were prepared according to the following general reaction schemes, the details of which are specified in the Examples. The starting materials and catalysts were purchased from Aldrich Chemical Company.

Structure VI, 3-heptylbicyclo[3.2.1]oct-6-en-2-one was prepared according to the following reactions scheme.

First 2-methylene nonanal (II) was prepared as follows,

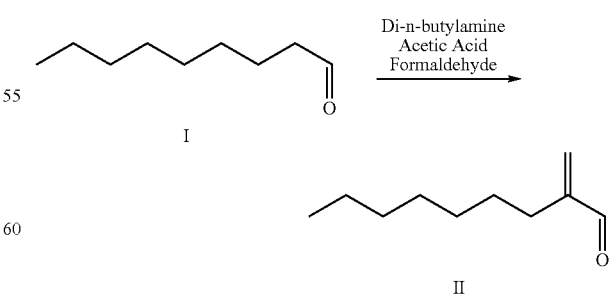

Then 2-heptylbicyclo[2.2.1]hept-5-ene-2-carbaldehyde (III) was prepared accordingly, with dicyclopentadiene (Aldrich Chemicals) used as a catalyst,

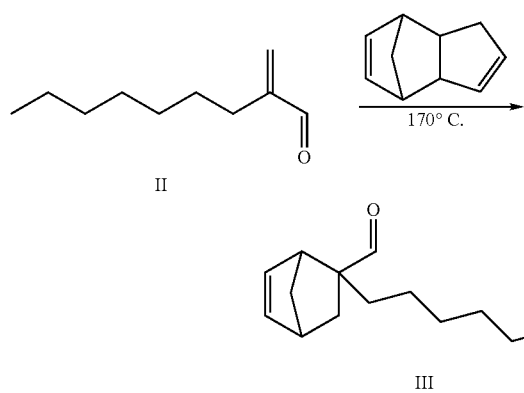

3-heptylbicyclo[3.2.1]oct-6-en-2-one (IV) was provided accordingly,

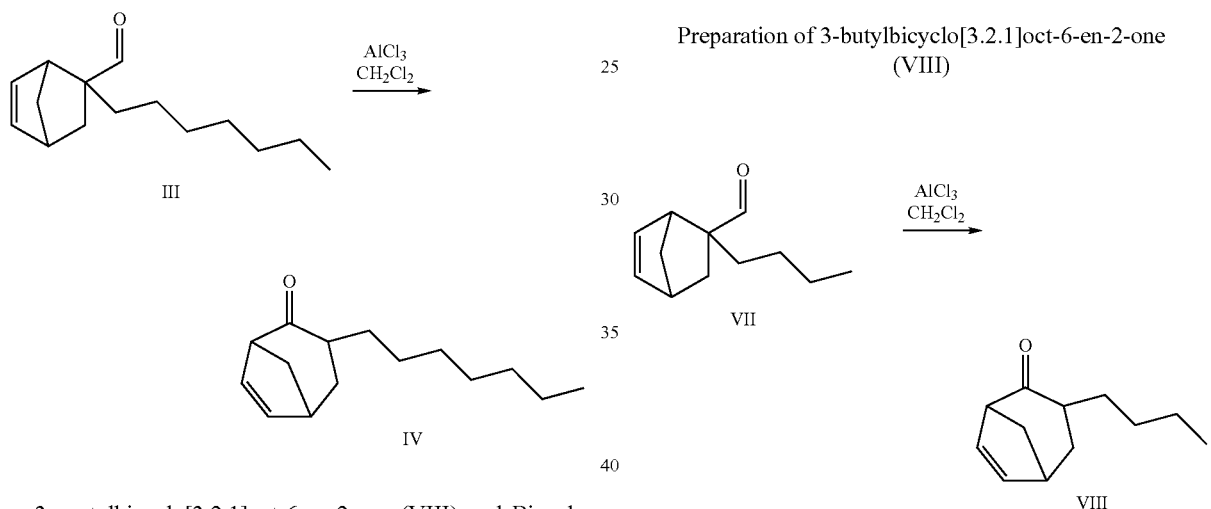

3-pentylbicyclo[3.2.1]oct-6-en-2-one (VIII) and Bicyclo[3.2.1]octan-2-one, 3-butyl (IX) were prepared according to the general reaction scheme below, the details of the reaction are provided in the Examples.

Preparation of 2-methylene hexanal (V)

Preparation of 2-pentylbicyclo[2.2.1]hept-5-ene-2-carbaldehyde (VII)

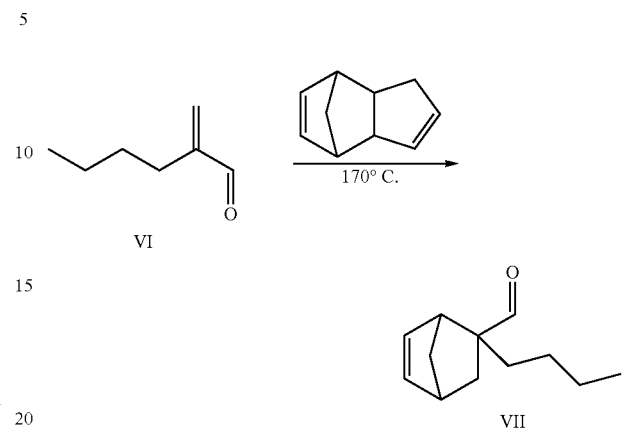

Preparation of 3-butylbicyclo[3.2.1]oct-6-en-2-one (VIII)

Preparation of Bicyclo[3.2.1]octan-2-one, 3-butyl (IX)

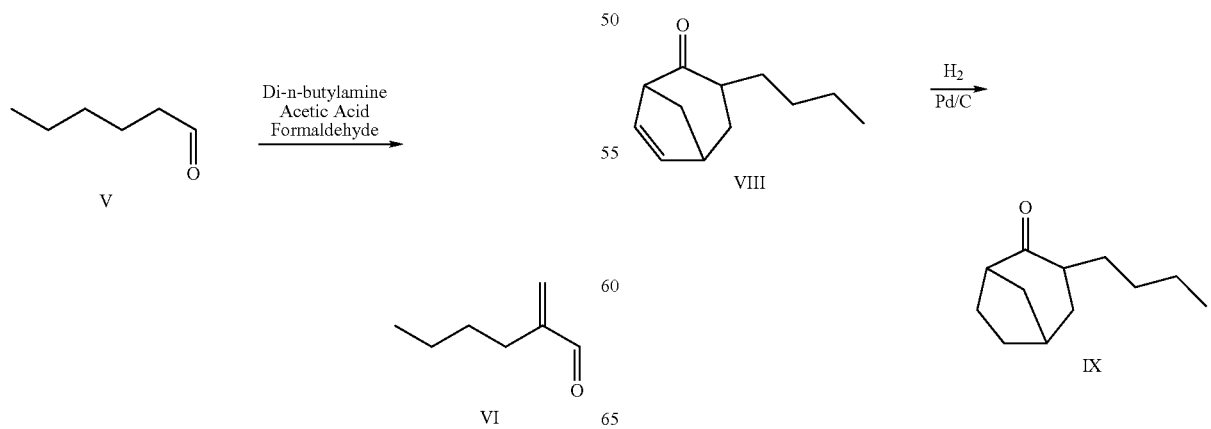

3-hexylbicyclo[3.2.1]oct-6-en-2-one (XIII) was prepared according to the following general reaction scheme.

First 2-methylene octanal (X) was prepared,

Preparation of Spiro[bicyclo[3.2.1]oct-6-ene-2,2'-[1,3]dioxoloane], 3-hexyl (XIV)

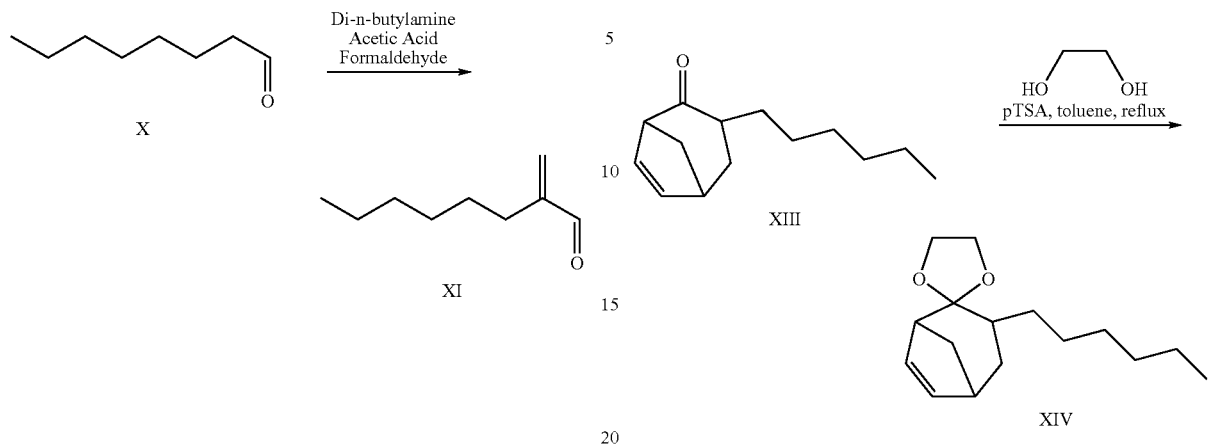

Then 2-hexylbicyclo[2.2.1]hept-5-ene-2-carbaldehyde (XII) was prepared as follows, 3-pentylbicyclo[3.2.1]oct-6-en-2-one (XV) and Bicyclo[3.2.1]ocatn-2-one, 3-pentyl (XVI) were prepared according to the general reaction scheme, First 2-methylene heptanal (XVI) was prepared,

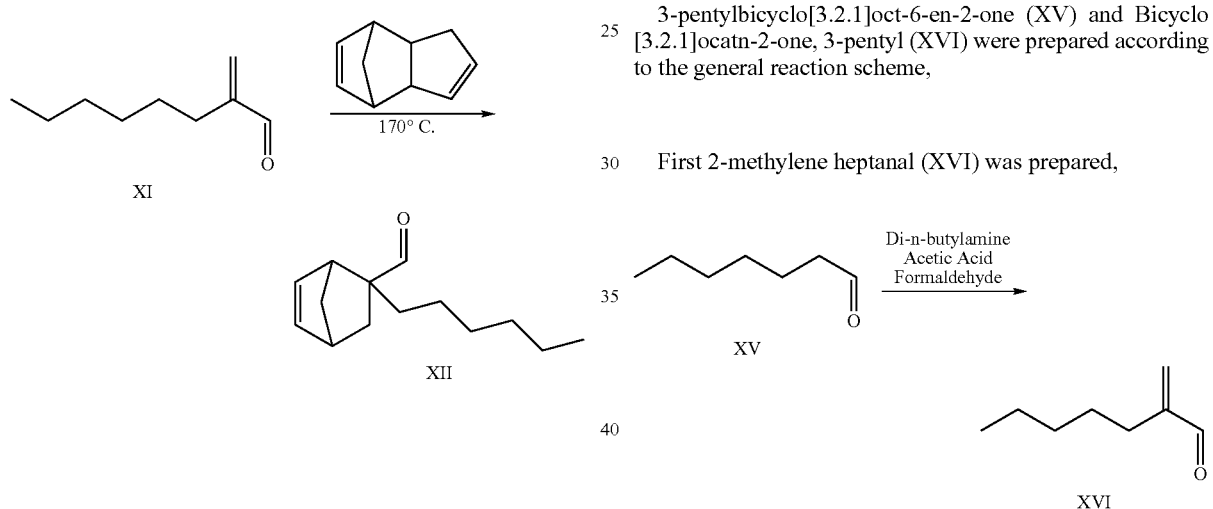

Preparation of 3-hexylbicyclo[3.2.1]oct-6-en-2-one (XIII)

Then, 2-pentylbicyclo[2.2.1]hept-5-ene-2-carbaldehyde (XVII) was prepared,

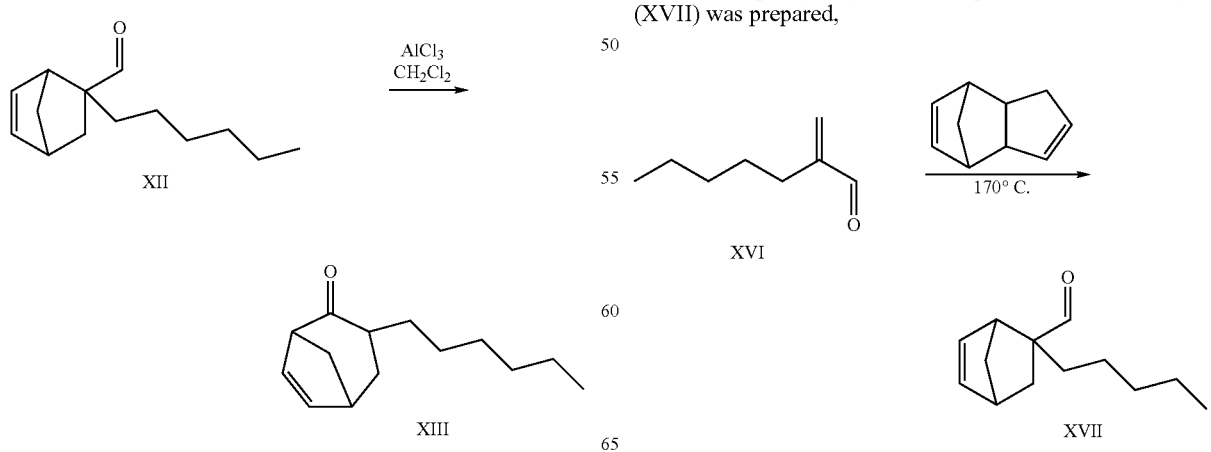

3-pentylbicyclo[3.2.1]oct-6-en-2-one (XVIII) was prepared as follows,

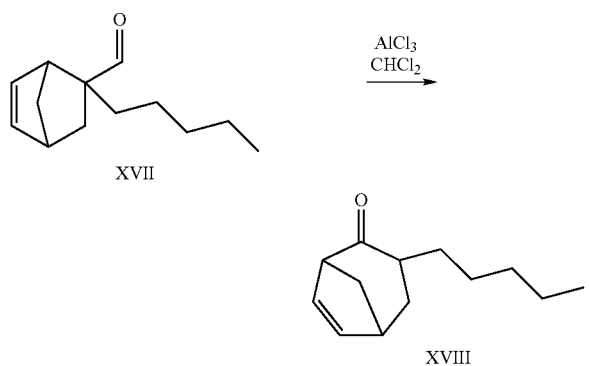

Finally, Bicyclo[3.2.1]octan-2-one, 3-pentyl (XIX) was prepared accordingly,

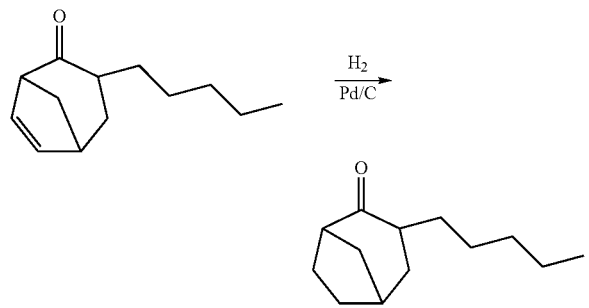

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

The compounds of the present invention possess the following fragrance notes:

Structure IV, 3-heptylbicyclo[3.2.1]oct-6-en-2-one, possesses weak, methyl salicylate like and slightly fruity fragrance notes;

Structure VIII, 3-butylbicyclo[3.2.1]oct-6-en-2-one, possesses fruity, slight green, herbal and celery notes;

Structure IX, Bicyclo[3.2.1]octan-2-one, 3-butyl, possesses coconut, lactonic, woody, minty, jasmonic cis like, anisic and tuberose notes;

Structure XIII, 3-hexylbicyclo[3.2.1]oct-6-en-2-one, possesses fruity, floral, sweet and aldehydic fragrance notes;

Structure XVIII, 3-pentylbicyclo[3.2.1]oct-6-en-2-one, possesses anisic, fruity, spicy, mossy, herbal and celery fragrance notes;

Structure XIX, Bicyclo[3.2.1]octan-2-one, 3-pentyl, possesses sweet, slight, anisic, floral and celery notes; and Structure XIV, Spiro[bicyclo[3.2.1]oct-6-ene-2,2'-[1,3]dioxoloane], 3-hexyl, possesses piney and weak fragrance notes.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers and polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

When used in a fragrance formulation this ingredient provides freshness making the fragrance top notes more desirable and noticeable. It also has a spicy peppery odor which is very commonly used in men's fragrances added for fragrance appropriateness and desirability. The woody part of it is very useful in both men's and women's fragrances adding body and substantivity to the finished product. All of these odor qualities found in this material assist in beautifying and enhancing the finished accord improving the performance of the other materials in the fragrance. The floral of it will beautify as well and makes the fragrance more desirable and add the perception of value. There is also the fruity side of it which is found in many fragrances today which happens to be very trendy, especially for the younger consumer.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, L is understood to be liter, Kg is understood to be kilogram, and g be gram. IFF as used in the examples is understood to mean International Flavors & Fragrances Inc., New York, N.Y., USA.

EXAMPLE I

Process for the Preparation of 3-heptylbicyclo[3.2.1]oct-6-en-2-one (VI)

Preparation of 2-methylene nonanal (II)

A 5-liter flask fitted with an overhead stirrer and condenser was charged with di-N-butyl amine (61 g, 0.47 mol) and acetic acid (56 g, 0.9 mol). Roughly 900 ml of 37% formaldehyde solution in water (351 g formaldehyde, 11.7 mol) was then added and the resulting solution was heated to 50° C. with stirring. After this temperature was reached nonanal (1000 g, 7.0 mol) was fed in over about 2 h. A slight exotherm was noticed during the feed. Monitoring by GC showed the consumption of nonanal and the production of 2-methylene nonanal, finally reaching roughly 95% conversion after the addition was complete. The reaction mixture was allowed to cool to room temperature, poured into a separatory funnel, and washed once with 5% HCl solution. The organic layer was then washed once with saturated sodium bicarbonate, then taken directly on to the next step.

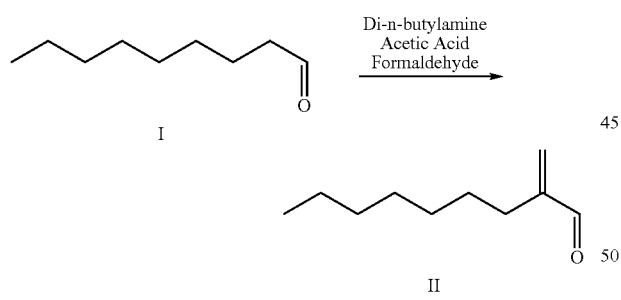

Preparation of 2-heptylbicyclo[2.2.1]hept-5-ene-2-carbaldehyde (III)

The material from the previous step (868 g, 5.6 mol) was loaded into a 2-liter stainless steel pressure reactor along with dicyclopentadiene (443 g, 3.4 mol). The pressure reactor was sealed and the mixture was heated to 170° C. with stirring. Samples taken from the reactor showed the generation of a new peak in eventual 60% conversion, along with several smaller peaks. After two hours at this temperature the material was cooled to room temperature and refluxed at 110° C. under vacuum in order to remove lower-boiling impurities. This treatment resulted in 909 g material, of roughly 75% purity. The material was taken on to the next step without further purification.

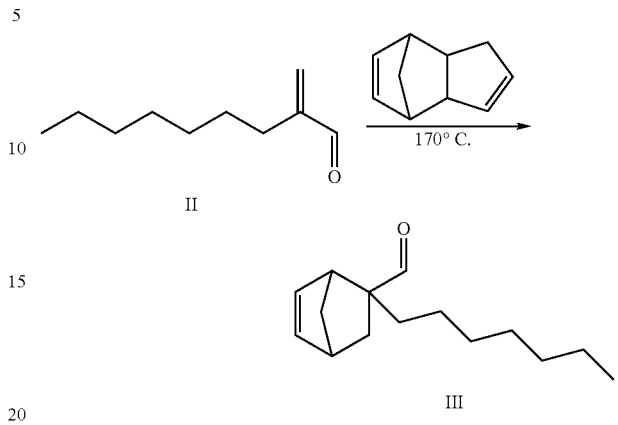

Preparation of 3-heptylbicyclo[3.2.1]oct-6-en-2-one (IV)

Aluminum chloride (279 g, 2 mol) was dissolved in one liter of methylene chloride in a three liter flask and cooled to 0° C. Structure III (909 g, 4.1 mol) was loaded into an addition funnel and fed into the reaction flask while maintaining this temperature. After two hours the reaction was complete as shown by GC measurements. The reaction mixture was then poured onto ice and 10% sulfuric acid, and the organic layers were separated and washed once with 10% sodium hydroxide solution. The methylene chloride solvent was then removed under reduced pressure, and the resulting oil was purified by simple distillation to yield 260 g (28% yield) of IV. Structure IV, 3-heptylbicyclo[3.2.1]oct-6-en-2-one, possesses weak, methyl salicylate like and slightly fruity fragrance notes.

$^1$H NMR (CDCl$_3$, 500 MHz): 0.87 ppm (t, 3H, J=6.72 Hz), 1.14-1.38 ppm (m, ~50% of 1H+11H), 1.43-1.50 ppm (m, ~50% of 1H), 1.75-1.83 ppm (m, ~50% of 1H+1H), 2.39-2.42 ppm (m, ~50% of 1H), 2.45-2.49 ppm (m, ~50% of 1H), 2.62-2.70 ppm (m, ~50% of 1H), 2.76-2.82 ppm (m, ~50% of 1H), 2.82-2.85 ppm (m, ~50% of 1H), 3.00-3.02 ppm (m, ~50% of 1H), 3.04-3.06 ppm (m, ~50% of 1H), 5.78-5.82 ppm (m, ~50% of 1H), 6.03-6.06 ppm (m, ~50% of 1H), 6.20-6.26 ppm (m, 1H).

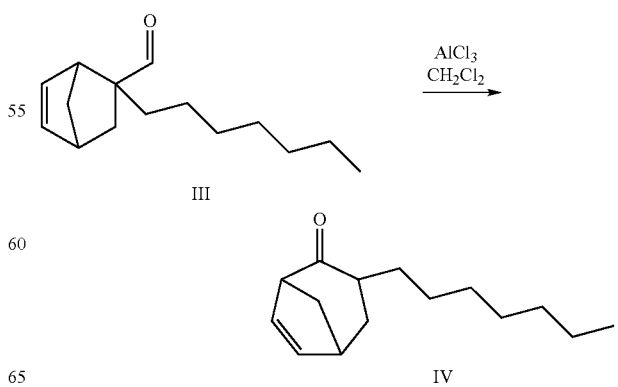

EXAMPLE II

Process for the Preparation of 3-pentylbicyclo[3.2.1]oct-6-en-2-one (VIII) and Bicyclo[3.2.1]octan-2-one, 3-butyl (IX)

Preparation of 2-methylene hexanal (V)

A 5-liter flask fitted with an overhead stirrer and condenser was charged with di-N-butyl amine (77 g, 0.59 mol) and acetic acid (72 g, 1.2 mol). Roughly 1100 ml of 37% formaldehyde solution in water (450 g formaldehyde, 15 mol) was then added and the resulting solution was heated to 50° C. with stirring. After this temperature was reached hexanal (1000 g, 10 mol) was fed in over about 2 hours. A slight exotherm was noticed during the feed. Monitoring by GC showed the consumption of hexanal and the production of 2-methylene hexanal, finally reaching roughly 95% conversion after the addition was complete, although only 60% was the desired product. The reaction mixture was allowed to cool to room temperature, poured into a separatory funnel, and washed once with 5% HCl solution. The organic layer was then washed once with saturated sodium bicarbonate, then taken directly on to the next step.

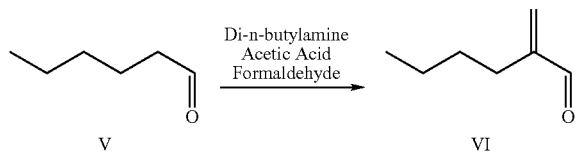

Preparation of 2-pentylbicyclo[2.2.1]hept-5-ene-2-carbaldehyde (VII)

The material from the previous step (727 g, 6.5 mol) was loaded into a 2-liter stainless steel pressure reactor along with dicyclopentadiene (511 g, 3.9 mol). The pressure reactor was sealed and the mixture was heated to 170° C. with stirring. Samples taken from the reactor showed the generation of a new peak in eventual 60% conversion, along with several smaller peaks. After two hours at this temperature the material was cooled to room temperature and distilled using a simple distillation apparatus. The final yield of material was 570 g, or 49% yield.

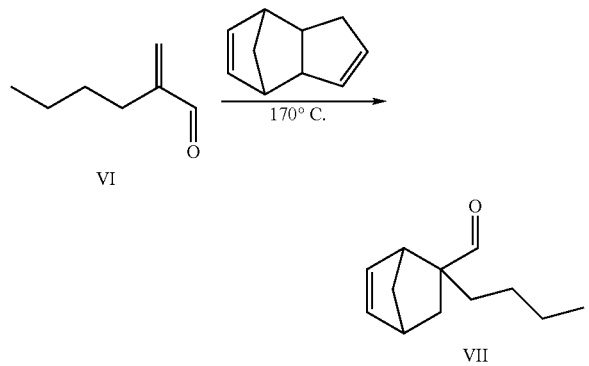

Preparation of 3-butylbicyclo[3.2.1]oct-6-en-2-one (VIII)

Compound VII (570 g, 3.2 mol) was loaded into a 3-liter round bottom flask fitted with a condenser and an overheard stirrer. This was followed by one liter of methylene chloride. The resulting solution was cooled to −50° C. using a dry ice bath. After this temperature was reached, anhydrous aluminum chloride (215 g, 1.6 mol) was added in one portion. The light yellow solution changed color to orange, then dark red with a simultaneous increase in reaction temperature, up to roughly −30° C. A GC sample taken after the addition was complete showed little reaction. The reaction temperature was allowed to gradually increase to 15° C., and GC monitoring showed the complete consumption of start material after one hour at this temperature. The reaction mixture was then poured onto ice and 10% sulfuric acid, and the organic layers were separated and washed once with 10% sodium hydroxide solution. The methylene chloride solvent was then removed under reduced pressure, and the resulting oil was purified by simple distillation to yield 224 g (49% yield) of VIII.

Structure VIII, 3-butylbicyclo[3.2.1]oct-6-en-2-one, possesses fruity, slight green, herbal and celery notes.

$^1$H NMR (CDCl$_3$, 500 MHz): 0.88 ppm (t, 3H, J=7.03 Hz), 1.18-1.38 ppm (m, 5H+~20% of 1H), 1.44-1.50 ppm (m, ~80% of 1H), 1.75-1.85 (m, ~80% of 1H), 1.84 ppm (d, 1H, J=11.1 Hz), 1.94-1.99 ppm (m, ~80% of 1H), 2.12-2.25 ppm (m, ~20% of 3H), 2.39-2.52 (m, 1H), 2.64-2.71 (m, ~80% of 1H), 2.77-2.88 ppm (m, 1H), 3.00-3.07 ppm (m, 1H), 5.78-5.82 ppm (m, ~20% of 1H), 6.02-6.07 ppm (dd, ~80% of 1H, J=5.29, 2.82 Hz), 6.19-6.28 ppm (dd, 1H, J=5.55, 2.65 Hz).

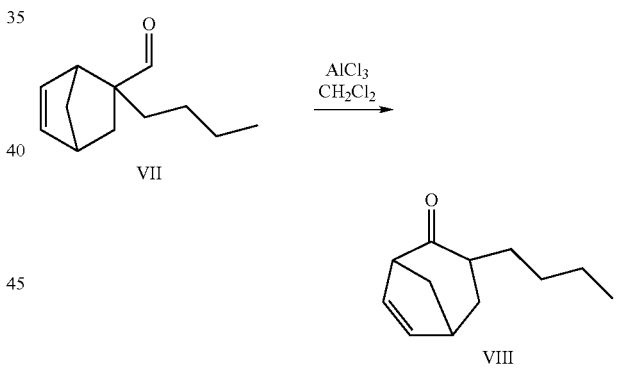

Preparation of Bicyclo[3.2.1]octan-2-one, 3-butyl (IX)

Compound VIII (100 g, 0.56 mol) was placed in a stainless steel autoclave with isopropanol (50 g) and palladium on carbon (1 g). The resulting mixture was placed under 300 psi of hydrogen gas, and heated at 100° C. until gas uptake ceased. The resulting material was removed from the autoclave, filtered, and distilled to yield a pure sample of IX.

Structure IX, Bicyclo[3.2.1]octan-2-one, 3-butyl, possesses coconut, lactonic, woody, minty, jasmonic cis like, anisic and tuberose notes 1H NMR (CDCl3, 500 MHz), 0.99 ppm (t, 3H, J=7.11 Hz), 1.11-1.34 ppm (m, 6H), 1.65-1.75 ppm (m, 3H), 1.76-1.88 ppm (m, 3H), 1.90-2.02 ppm (m, 2H), 2.24-2.34 ppm (m, 1H), 2.39-2.44 ppm (m, 1H), 2.70-2.74 ppm (m, 1H).

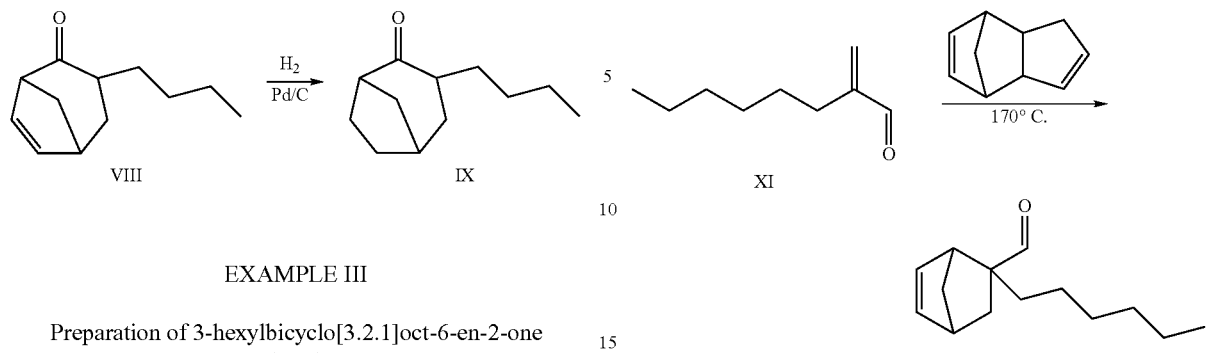

EXAMPLE III

Preparation of 3-hexylbicyclo[3.2.1]oct-6-en-2-one (XIII)

Preparation of 2-methylene octanal (X)

A 5-liter flask fitted with an overhead stirrer and condenser was charged with di-N-butyl amine (61 g, 0.47 mol) and acetic acid (56 g, 0.9 mol). Roughly 900 ml of 37% formaldehyde solution in water (351 g formaldehyde, 11.7 mol) was then added and the resulting solution was heated to 50° C. with stirring. After this temperature was reached octanal (1000 g, 7.0 mol) was fed in over about 2 h. A slight exotherm was noticed during the feed. Monitoring by GC showed the consumption of octanal and the production of 2-methylene octanal, finally reaching roughly 95% conversion after the addition was complete. The reaction mixture was allowed to cool to room temperature, poured into a separatory funnel, and washed once with 5% HCl solution. The organic layer was then washed once with saturated sodium bicarbonate, then taken directly on to the next step.

Preparation of 2-hexylbicyclo[2.2.1]hept-5-ene-2-carbaldehyde (XII)

The material from the previous step (840 g, 5.9 mol) was loaded into a 2-liter stainless steel pressure reactor along with dicyclopentadiene (468 g, 3.5 mol). The pressure reactor was sealed and the mixture was heated to 170° C. with stirring. Samples taken from the reactor showed the generation of a new peak in eventual 60% conversion, along with several smaller peaks. After two hours at this temperature the material was cooled to room temperature and purified via simple distillation. This treatment resulted in 548 g material. The material was taken on to the next step without further purification.

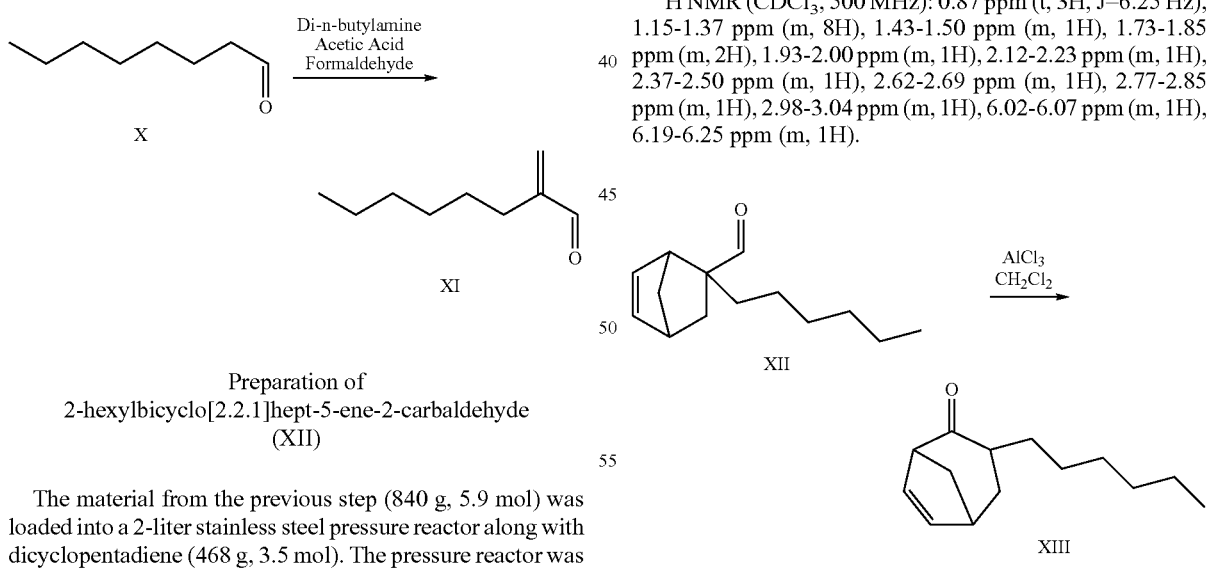

Preparation of 3-hexylbicyclo[3.2.1]oct-6-en-2-one (XIII)

Compound XII (236 g, 1.1 mol) was loaded into a three liter flask and dissolved in one liter of toluene. This mixture was then cooled to −30° C. Aluminum chloride (77 g, 0.56 mol) was then added in one portion. The reaction mixture exothermed moderately and changed color to light orange. The temperature was allowed to rise to −15° C., then held for 3.5 hours. After this time the reaction was complete as shown by GC measurements. The reaction mixture was then poured onto ice and 25% sulfuric acid, and the organic layers were separated and washed once with 10% sodium hydroxide solution. The methylene chloride solvent was then removed under reduced pressure, and the resulting oil was purified by simple distillation to yield 163 g (69% yield) of XIII.

Structure XIII, 3-hexylbicyclo[3.2.1]oct-6-en-2-one, possesses fruity, floral, sweet and aldehydic fragrance notes.

$^1$H NMR (CDCl$_3$, 500 MHz): 0.87 ppm (t, 3H, J=6.25 Hz), 1.15-1.37 ppm (m, 8H), 1.43-1.50 ppm (m, 1H), 1.73-1.85 ppm (m, 2H), 1.93-2.00 ppm (m, 1H), 2.12-2.23 ppm (m, 1H), 2.37-2.50 ppm (m, 1H), 2.62-2.69 ppm (m, 1H), 2.77-2.85 ppm (m, 1H), 2.98-3.04 ppm (m, 1H), 6.02-6.07 ppm (m, 1H), 6.19-6.25 ppm (m, 1H).

Preparation of Spiro[bicyclo[3.2.1]oct-6-ene-2,2'-[1,3]dioxoloane], 3-hexyl (XIV)

Compound XIII (70 g, 0.33 mol) was placed in a 2 liter round bottom flask equipped with a bidwill trap. 500 mL of toluene, 700 mg of pTSA (1 wt %), and ethylene glycol (21 g, 0.33 mol) was added. The mixture was heated to reflux and freed water was removed via the bidwill. After the mixture reached roughly 90% conversion, the material was cooled to room temperature and basified by the addition of 100 mL of 10% NaOH solution. The organic layer was then separated from the water layer, reduced in volume, and the material was purified by fractional distillation to yield a pure sample of XIV.

Structure XIV, Spiro[bicyclo[3.2.1]oct-6-ene-2,2'-[1,3]dioxoloane], 3-hexyl, possesses piney and weak fragrance notes

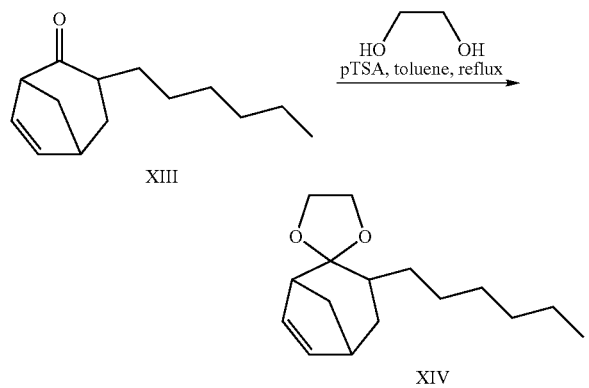

XIII

XIV

EXAMPLE IV

Preparation of 3-pentylbicyclo[3.2.1]oct-6-en-2-one (XV) and Bicyclo[3.2.1]ocatn-2-one, 3-pentyl (XVI)

Preparation of 2-methylene heptanal (XVI)

A 3-liter three-neck flask fitted with an overhead stirrer and condenser was charged with di-N-butyl amine (33 g, 0.25 mol) and acetic acid (31 g, 0.5 mol). Roughly 500 ml of 33% formaldehyde solution in water (178 g formaldehyde, 5.9 mol) was then added and the resulting solution was heated to 50° C. with stirring. After this temperature was reached heptanal (500 g, 4.3 mol) was fed in over about 1.5 h. A slight exotherm was noticed during the feed. Monitoring by GC showed the consumption of heptanal and the production of 2-methylene heptanal, finally reaching roughly 95% conversion after the addition was complete. The reaction mixture was allowed to cool to room temperature, poured into a separatory funnel, and washed once with 5% HCl solution. The organic layer was then washed once with saturated sodium carbonate, then taken directly on to the next step.

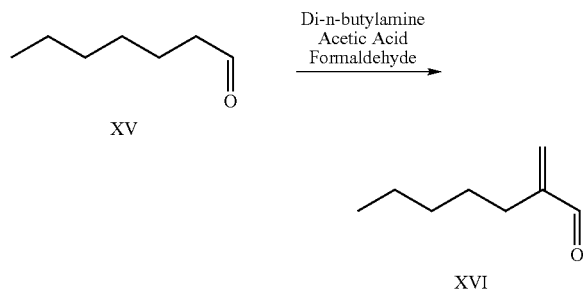

XV

XVI

Preparation of 2-pentylbicyclo[2.2.1]hept-5-ene-2-carbaldehyde (XVII)

The material from the previous step (553 g, 4.3 mol) was loaded into a 2-liter stainless steel pressure reactor along with dicyclopentadiene (343 g, 2.6 mol). The pressure reactor was sealed and the mixture was heated to 170° C. with stirring. Samples taken from the reactor showed the generation of a new peak in eventual 60% conversion, along with several smaller peaks. After two hours at this temperature the material was cooled to room temperature and distilled using a fractional distillation apparatus. The final yield of material was 217 g, or 26% yield.

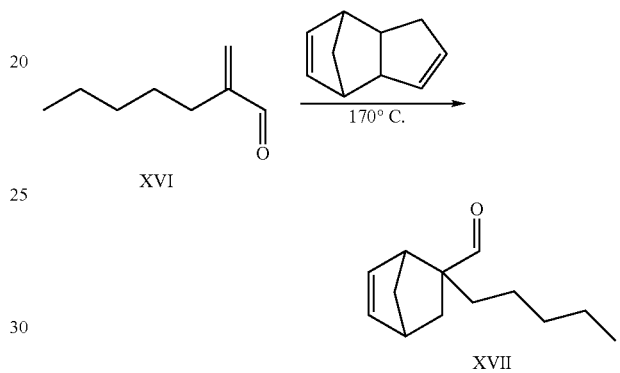

XVI

XVII

Preparation of 3-pentylbicyclo[3.2.1]oct-6-en-2-one (XVIII)

Compound XVII (217 g, 1.1 mol) was loaded into a 2-liter round bottom flask fitted with a condenser and an overheard stirrer. This was followed by one liter of methylene chloride. The resulting solution was cooled to 0° C. using a dry ice bath. After this temperature was reached, anhydrous aluminum chloride (153 g, 1.1 mol) was added in one portion. The light yellow solution changed color to orange, then dark red with a simultaneous increase in reaction temperature, up to the boiling point of methylene chloride. A GC sample taken after the reaction began to cool showed the complete consumption of start material and the formation of a new product. The reaction was then poured onto ice, and the organic layers were separated and washed once with 10% sodium hydroxide solution. The methylene chloride solvent was then removed under reduced pressure, and the resulting oil was purified by simple distillation to yield 100 g (46% yield) of XVIII.

Structure XVIII, 3-pentylbicyclo[3.2.1]oct-6-en-2-one, possesses anisic, fruity, spicy, mossy, herbal and celery fragrance notes.

$^1$H NMR (CDCl$_3$, 500 MHz): 0.87 ppm (t, 3H, J=7.05 Hz), 1.16-1.36 ppm (m, 8H), 1.76-1.83 ppm (m, 1H), 2.11-2.24 ppm (m, 3H), 2.44-2.50 ppm (m, 1H), 2.78 (s, 1H), 3.05 ppm (t, 1H, J=3.69 Hz), 5.80 ppm (dd, 1H, J=5.12, 3.31 Hz), 6.24 (dd, 1H, J=5.29, 2.91 Hz).

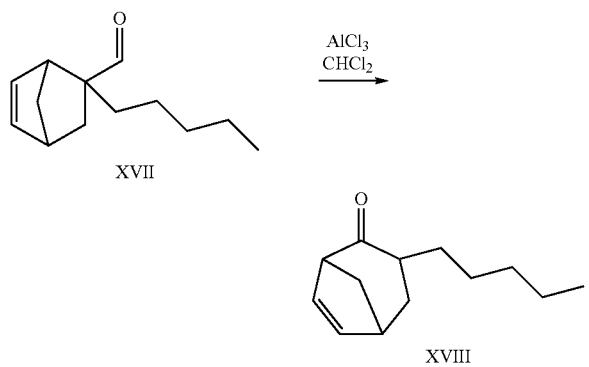

Preparation of Bicyclo[3.2.1]octan-2-one, 3-pentyl (XIX)

Compound XVIII (130 g, 0.67 mol) was placed in a stainless steel autoclave with 30 g isopropanol and 1.5 g palladium on carbon. The mixture was placed under 300 psi of hydrogen gas. The mixture was then heated at 100° C. until gas uptake ceased. The mixture was then removed from the autoclave, filtered, and distilled to yield a pure sample of XIX.

Structure XIX, Bicyclo[3.2.1]octan-2-one, 3-pentyl, possesses sweet, slight, anisic, floral and celery notes.

$^1$H NMR (CDCl$_3$, 500 MHz): 0.88 ppm (t, 3H, J=6.89 Hz), 1.10-1.18 ppm (m, 1H), 1.19-1.37 ppm (m, 7H), 1.65-1.89 ppm (m, 6H), 1.90-2.03 ppm (m, 2H), 2.25-2.34 ppm (m, 1H), 2.41-2.45 ppm (m, 1H), 2.73 ppm (t, 1H, J=5.62 Hz).

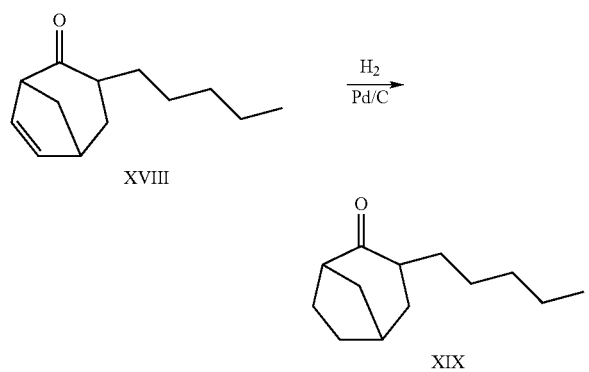

EXAMPLE V

Fragrance Formulation Containing Bicyclo[3.2.1]octan-2-one, 3-butyl (II)

| Fragrance ingredient | parts by wt. |
|---|---|
| Acetald DEA | 0.28 |
| Ald C-10 | 0.70 |
| Allyl amyl glycolate | 1.40 |
| Benz acet | 0.70 |
| Calone cam 1% dpg | 1.40 |
| Coumarin | 0.28 |

-continued

| Fragrance ingredient | parts by wt. |
|---|---|
| Cyclobutanate | 0.28 |
| Dihydro myrcenol | 6.99 |
| Dimeth benz carb acet | 6.99 |
| Eth vanillin | 0.14 |
| Eth-2-meth buty | 5.59 |
| Fleuranil 10% dpg | 1.40 |
| Bicyclo[3.2.1]octan-2-one, 3-butyl (II) | 5.00 |
| Galaxolide 50 pct dpg | 6.99 |
| Galbascone 10% dpg | 0.14 |
| Hexyl buty | 1.40 |
| Hexyl cinn ald | 6.99 |
| Ionol | 0.14 |
| Iso E super | 6.99 |
| Koavone | 1.40 |
| Mandarin oil hp | 2.80 |
| Mango ester 0.01 pct dpg | 1.40 |
| Meth anth (USDEA) | 0.70 |
| Nebulone | 6.99 |
| Orange oil fla | 2.80 |
| Prenyl acet | 4.20 |
| Trisamber 1% dpg | 0.70 |
| Undecalactone gamma | 1.40 |
| Undecavertol | 2.69 |
| Verdox | 13.99 |
| Vertoliff | 6.99 |
| Vivaldie | 0.14 |
| Total: | 100.00 |

In this case, the presence of the claimed compound enhances the fruity and floral aspects of the fragrance composition.

EXAMPLE VI

Fragrance Formulation Containing Bicyclo[3.2.1]ocatn-2-one, 3-pentyl (IV)

| Fragrance Ingredient | parts by wt. |
|---|---|
| Acalea | 3.7 |
| Ald C-8 | 0.14 |
| Applelide | 6.89 |
| Benz acet | 3.45 |
| Banz alc | 6.89 |
| Benz prop | 3.45 |
| Citronellol Coeur | 6.89 |
| Cyclamal extra | 0.69 |
| Cyclaprop | 1.03 |
| Dimeth benz carb buty | 8.27 |
| Eth Caproate | 0.69 |
| Eth Vanillin | 0.07 |
| Eth-2-meth buty | 0.14 |
| Floralozone | 1.38 |
| Bicyclo[3.2.1]ocatn-2-one, 3-pentyl (IV) | 5.00 |
| Geranyl acet pure | 2.07 |
| Helional | 0.14 |
| Hexalon | 0.69 |
| Hexenyl sal, cis-3 | 0.28 |
| Hexyl cinn ald | 4.13 |
| Hexyl sal | 0.07 |
| Iso cyclemone E | 0.41 |
| Kharismal | 4.35 |
| Lilial | 6.89 |
| Linalool syn | 5.51 |
| Linalyl acet | 1.38 |
| Meth cinnamate | 0.69 |
| Meth Ionone alpha extra | 0.34 |
| Muguesia | 2.07 |
| Nerol Coeur | 3.45 |

-continued

| Fragrance Ingredient | parts by wt. |
| --- | --- |
| Neryl acet A | 0.14 |
| Ocimene | 0.07 |
| Orange oil nova decol | 2.76 |
| Peach ald Coeur | 0.69 |
| Phen eth alc white extra | 1.72 |
| Styralyl acet | 0.07 |
| Terpineol Coeur | 1.38 |
| Verdox | 5.17 |
| Vertenex | 6.85 |
| Total: | 100.00 |

In this case, the claimed compound enhances the fruity and floral aspects of the fragrance composition.

What is claimed is:

1. A method of improving, enhancing, or modifying a fragrance formulation through the addition of an olfactory acceptable amount of a compound:

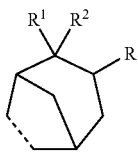

wherein the dotted line represents a possible single or double bond;
R is equal to a $C_3$-$C_7$ hydrocarbon moiety; and
$R^1$ and $R^2$ together are oxygen or form a closed ring structure represented by

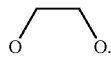

2. The method of claim 1, wherein R is equal to a $C_3$-$C_7$ hydrocarbon moiety, $R^1$ and $R^2$ together are equal to oxygen and the dotted line represents a single bond.

3. The method of claim 1, wherein R is equal to a $C_3$-$C_7$ hydrocarbon moiety, $R^1$ and $R^2$ together are equal to oxygen and the dotted line represents a double bond.

4. The method of claim 3, wherein R is equal to a $C_4H_9$ hydrocarbon moiety providing the compound 3-butylbicyclo[3.2.1]oct-6-en-2-one.

5. The method of claim 3, wherein R is equal to a $C_5H_{11}$ hydrocarbon moiety providing the compound 3-pentylbicyclo[3.2.1]oct-6-en-2-one.

6. The method of claim 1, wherein R is equal to a $C_3$-$C_7$ hydrocarbon moiety, $R^1$ and $R^2$ together may form a closed ring structure represented by

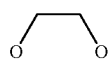

and the dotted line represents a double bond.

7. The method of claim 1, wherein R is equal to a $C_3$-$C_7$ hydrocarbon moiety, $R^1$ and $R^2$ together may form a closed ring structure represented by

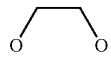

and the dotted line represents a single bond.

8. The method of claim 1, wherein the fragrance formulation is incorporated into a product selected from the group consisting of a perfume, a cologne, a toilet water, a cosmetic product, a personal care product, a fabric care product, a cleaning product, and an air freshener.

9. The method of claim 8, wherein the cleaning product is selected from the group consisting of a detergent, a dishwashing composition, a scrubbing compound, and a window cleaner.

10. The method of claim 1, wherein the olfactory acceptable amount is from about 0.005 to about 10 weight percent.

11. The method of claim 1, wherein the olfactory acceptable amount is from about 0.1 to about 8 weight percent.

12. The method of claim 1, wherein the olfactory acceptable amount is from about 0.5 to about 5 weight percent.

* * * * *